United States Patent
Beumer et al.

(10) Patent No.: US 9,567,286 B2
(45) Date of Patent: *Feb. 14, 2017

(54) FLAVOR AND FRAGRANCE FORMULATION (III)

(71) Applicant: DSM IP ASSETS B.V., Heerlen (NL)

(72) Inventors: Raphael Beumer, Basel (CH);
Johannes Tschumi, Basel (CH);
Michael Gressly, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,388

(22) PCT Filed: Oct. 7, 2013

(86) PCT No.: PCT/EP2013/070831
§ 371 (c)(1),
(2) Date: Mar. 23, 2015

(87) PCT Pub. No.: WO2014/056848
PCT Pub. Date: Apr. 17, 2014

(65) Prior Publication Data
US 2015/0246868 A1 Sep. 3, 2015

(30) Foreign Application Priority Data
Oct. 8, 2012 (EP) .................... 12187646

(51) Int. Cl.
| | | |
|---|---|---|
| C07C 69/708 | (2006.01) |
| A61K 8/34 | (2006.01) |
| A61Q 13/00 | (2006.01) |
| C07C 31/125 | (2006.01) |
| C07C 43/13 | (2006.01) |
| C11B 9/00 | (2006.01) |
| C07C 69/14 | (2006.01) |
| A61K 8/37 | (2006.01) |
| A61Q 19/00 | (2006.01) |
| A61L 9/01 | (2006.01) |
| A61Q 5/02 | (2006.01) |
| C07C 69/145 | (2006.01) |
| A61Q 5/12 | (2006.01) |
| A61Q 15/00 | (2006.01) |
| A61Q 19/10 | (2006.01) |
| C07C 29/17 | (2006.01) |
| C07C 33/025 | (2006.01) |
| C07C 41/26 | (2006.01) |
| C07C 67/40 | (2006.01) |
| C07C 69/003 | (2006.01) |
| C07C 69/007 | (2006.01) |
| C11D 3/20 | (2006.01) |
| C11D 3/50 | (2006.01) |
| C11D 11/00 | (2006.01) |

(52) U.S. Cl.
CPC .......... *C07C 69/708* (2013.01); *A23L 27/2026* (2016.08); *A23L 27/2028* (2016.08); *A61K 8/34* (2013.01); *A61K 8/342* (2013.01); *A61K 8/37* (2013.01); *A61L 9/01* (2013.01); *A61Q 5/02* (2013.01); *A61Q 5/12* (2013.01); *A61Q 13/00* (2013.01); *A61Q 15/00* (2013.01); *A61Q 19/00* (2013.01); *A61Q 19/10* (2013.01); *C07C 29/17* (2013.01); *C07C 31/125* (2013.01); *C07C 33/025* (2013.01); *C07C 41/26* (2013.01); *C07C 43/13* (2013.01); *C07C 67/40* (2013.01); *C07C 69/003* (2013.01); *C07C 69/007* (2013.01); *C07C 69/14* (2013.01); *C07C 69/145* (2013.01); *C11B 9/0015* (2013.01); *C11B 9/0019* (2013.01); *C11D 3/2017* (2013.01); *C11D 3/2027* (2013.01); *C11D 3/2068* (2013.01); *C11D 3/2093* (2013.01); *C11D 3/50* (2013.01); *C11D 11/0017* (2013.01); *A61K 2800/10* (2013.01)

(58) Field of Classification Search
CPC . A61Q 13/00; A23L 27/2026; A23L 27/2024; A61K 8/37; A61K 8/34; C11B 9/0015; C11B 9/0019; C11D 3/50; C11D 3/2093; C11D 3/2027; C07C 33/025; C07C 69/145; C07C 67/00; A23V 2002/00; A61L 9/01
See application file for complete search history.

(56) References Cited

U.S. PATENT DOCUMENTS

| | | |
|---|---|---|
| 4,517,991 A | 5/1985 | Boden |
| 2009/0257974 A1 | 10/2009 | Evans et al. |

FOREIGN PATENT DOCUMENTS

| | | | | |
|---|---|---|---|---|
| EP | 1 795 518 | | 6/2007 | |
| EP | 1795518 A1 | * | 6/2007 | ......... C07C 31/1333 |
| JP | 55-023977 | | 2/1980 | |
| JP | 55023977 A | * | 2/1980 | |
| JP | 62089800 A | * | 4/1987 | |

OTHER PUBLICATIONS

JP 62089800, Derwent English Abstract, Apr. 1987.*
Bernotiene et al., Chemija, 2007, vol. 18, pp. 38-43.*
(Continued)

*Primary Examiner* — Mark V Stevens
(74) *Attorney, Agent, or Firm* — Nixon & Vanderhye P.C.

(57) ABSTRACT

The present invention relates to the use of specific organic compounds as flavor and fragrance material. Furthermore the invention relates to new specific organic compounds, as well as to flavor and fragrance formulations comprising at least one of the specific organic compounds.

6 Claims, 1 Drawing Sheet

(56) References Cited

OTHER PUBLICATIONS

Suga, JP 55023977 A (Japanese Published Patent application), Machine English translation, aquired in Aug. 2016.*
Frey Detection of Synthetic Flavorant Addition to Some Essential Oils by Selected Ion Monitoring GC/MS, 1988, Developments in Food Science, vol. 18, pp. 517-524.*
International Search Report for PCT/EP2013/070831, mailed Jan. 29, 2014, 4 pages.

* cited by examiner

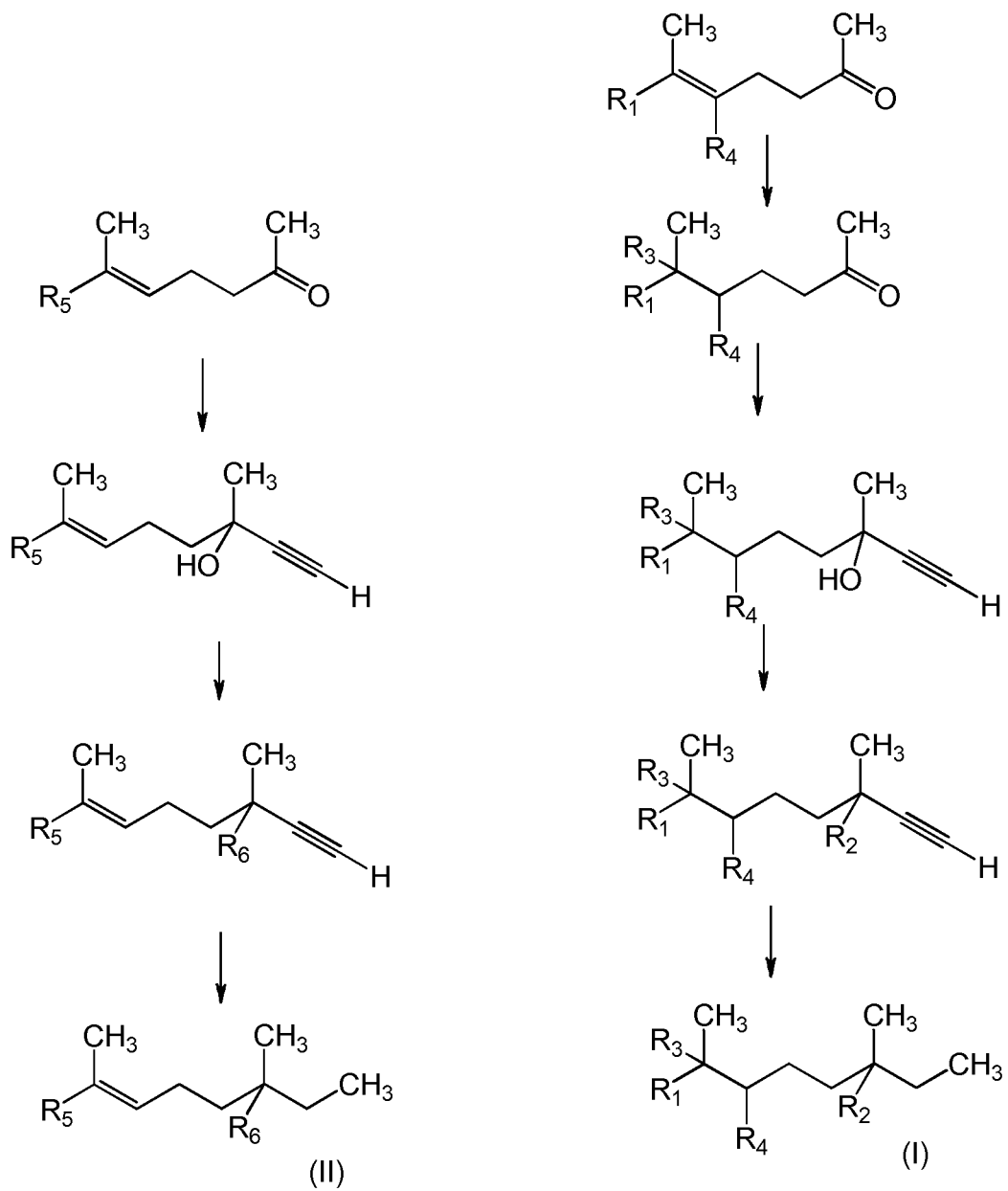

FLAVOR AND FRAGRANCE FORMULATION (III)

This application is the U.S. national phase of International Application No. PCT/EP2013/070831, filed 7 Oct. 2013, which designated the U.S. and claims priority to EP Application No. 12187646.0, filed 8 Oct. 2012, the entire contents of each of which are hereby incorporated by reference.

The present invention relates to the use of specific organic compounds as flavor and fragrance materials. Furthermore the invention relates to new specific organic compounds, as well as to flavor and fragrance formulations comprising at least one of the specific organic compounds.

In the flavor and fragrance industry there is always a need and demand for compounds that enhance, modify, improve or otherwise positively influence an odour note and therefore give perfumers or other persons the ability to create new fragrances for perfumes, colognes, personal care products, household products or any other products, which comprise flavor and fragrance materials.

Surprisingly it was found that the compounds of formula (I) and the compounds of formula (II) are very useful as flavor and fragrance material.

Therefore the present invention is related to the use of a compound of formula (I) and/or of a compound of formula (II)

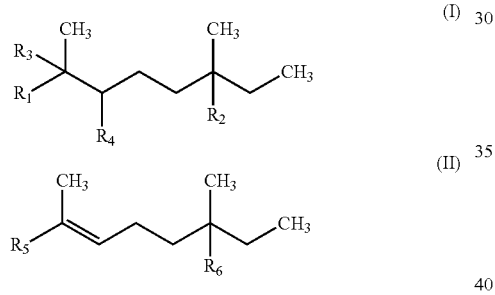

wherein
$R_1$ signifies —$CH_3$, —$CH_2CH_3$ or —$CH_2CH_2CH_3$, and
$R_2$ signifies —OH or —O(CO)$CH_3$, and
$R_3$ signifies —H, —OH or —O$CH_3$, and
$R_4$ signifies —H or —$CH_3$, and
$R_5$ signifies —$CH_3$, or —$CH_2CH_2CH_3$, and
$R_6$ signifies —OH or —O(CO)$CH_3$,
with the provisos that when
a) $R_1$ is —$CH_3$, then $R_2$ is not —OH and $R_3$ and $R_4$ are not —H, and
b) $R_5$ is —$CH_3$, then $R_6$ is not —OH,
as flavor and fragrance material.

Preferred is the use of at least one compound selected from the group consisting of the compounds of formulae (Ia)-(Ih) and of the compounds of formulae (IIa)-(IId)

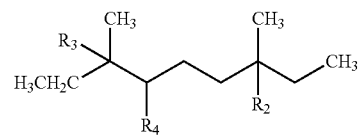

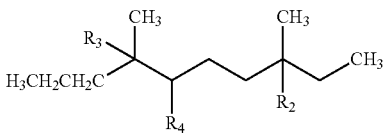

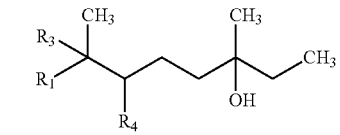

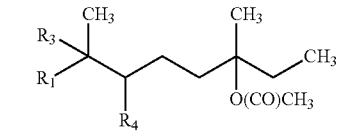

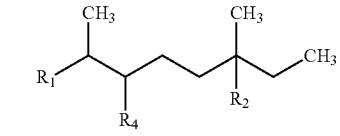

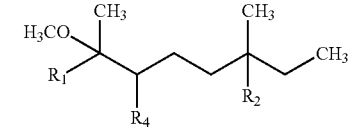

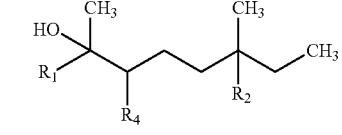

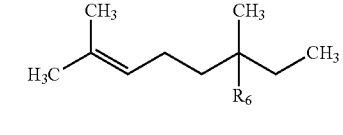

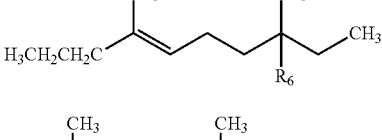

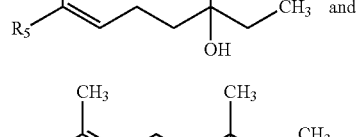

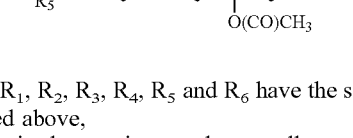

wherein $R_1$, $R_2$, $R_3$, $R_4$, $R_5$ and $R_6$ have the same meanings as defined above,
and wherein the provisos apply as well,
as flavor and fragrance material.

More preferred is the use of at least one compound selected from the group consisting of the compounds of formulae (III)-(XVII)

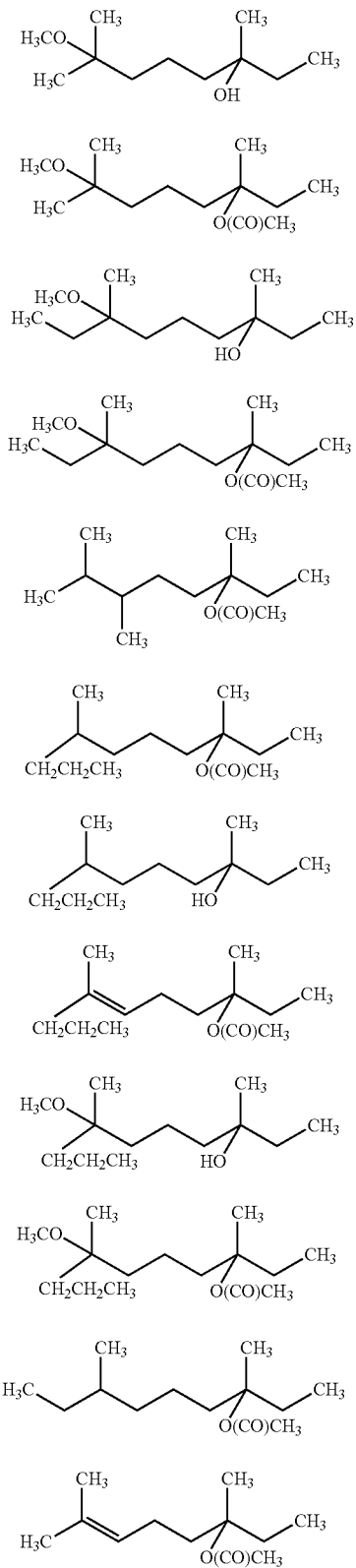

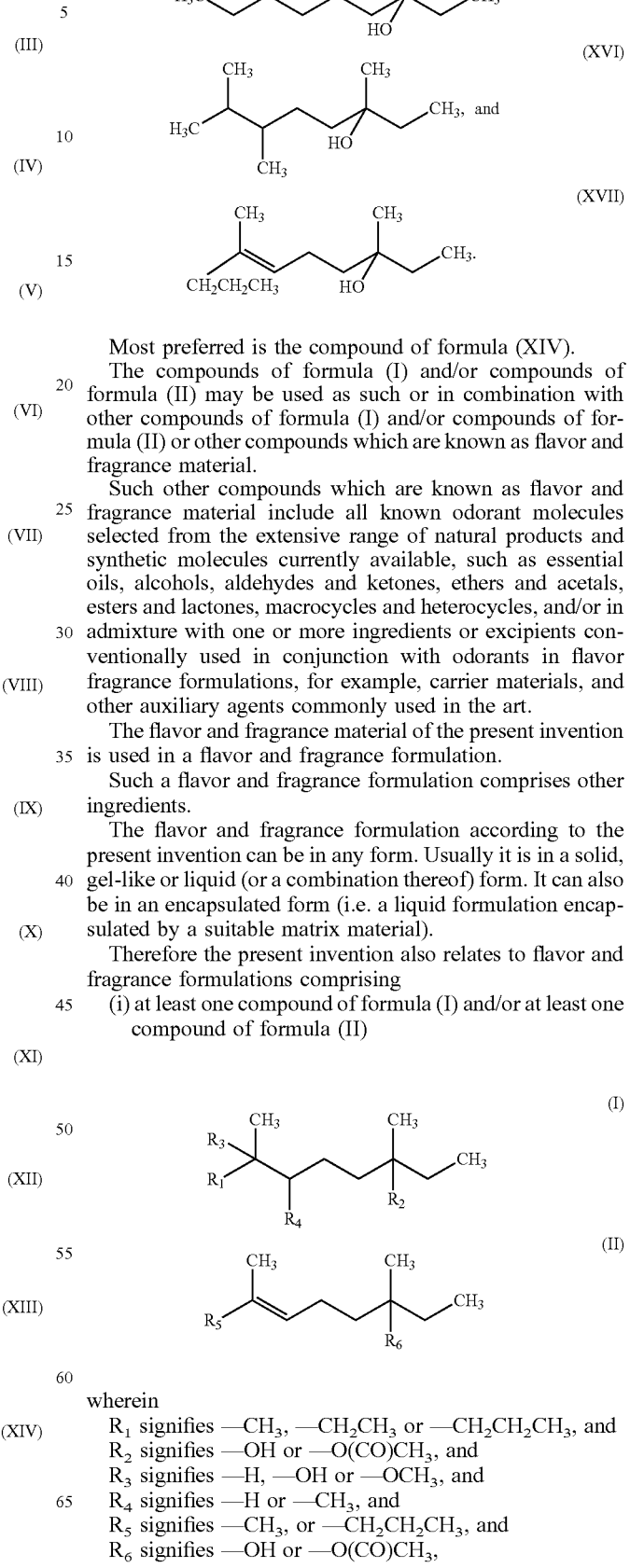

Most preferred is the compound of formula (XIV).

The compounds of formula (I) and/or compounds of formula (II) may be used as such or in combination with other compounds of formula (I) and/or compounds of formula (II) or other compounds which are known as flavor and fragrance material.

Such other compounds which are known as flavor and fragrance material include all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in flavor fragrance formulations, for example, carrier materials, and other auxiliary agents commonly used in the art.

The flavor and fragrance material of the present invention is used in a flavor and fragrance formulation.

Such a flavor and fragrance formulation comprises other ingredients.

The flavor and fragrance formulation according to the present invention can be in any form. Usually it is in a solid, gel-like or liquid (or a combination thereof) form. It can also be in an encapsulated form (i.e. a liquid formulation encapsulated by a suitable matrix material).

Therefore the present invention also relates to flavor and fragrance formulations comprising
(i) at least one compound of formula (I) and/or at least one compound of formula (II)

wherein
$R_1$ signifies —$CH_3$, —$CH_2CH_3$ or —$CH_2CH_2CH_3$, and
$R_2$ signifies —OH or —O(CO)$CH_3$, and
$R_3$ signifies —H, —OH or —O$CH_3$, and
$R_4$ signifies —H or —$CH_3$, and
$R_5$ signifies —$CH_3$, or —$CH_2CH_2CH_3$, and
$R_6$ signifies —OH or —O(CO)$CH_3$, with the provisos that when
a) $R_1$ is —$CH_3$, then $R_2$ is not —OH and $R_3$ and $R_4$ are not —H, and
b) $R_5$ is —$CH_3$, then $R_6$ is not —OH.

Preferred are flavor and fragrance formulations comprising at least one compound selected from the group consisting of the compounds of formulae (Ia)-(Ih) and of the compounds of formulae (IIa)-(IId)

wherein $R_1$, $R_2$, $R_3$, $R_4$, $R_5$ and $R_6$ have the same meanings as defined above, and wherein the provisos are applied as well.

More preferred are flavor and fragrance formulations comprising at least one compound selected from the group consisting of the compounds of formulae (III)-(XVII)

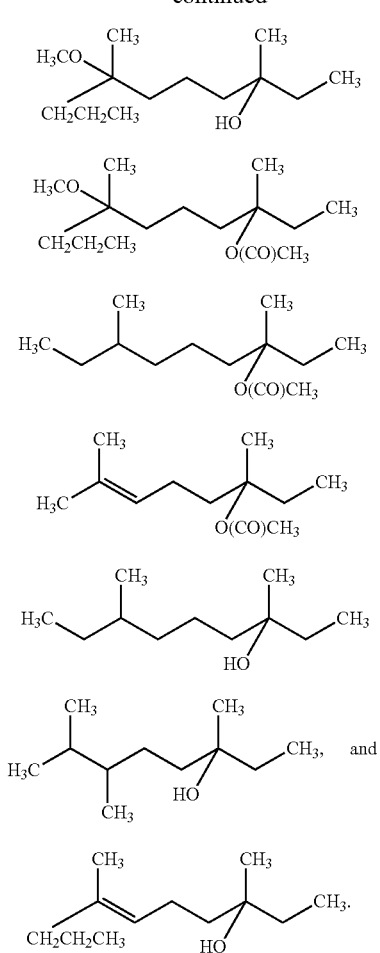

(XI)
(XII)
(XIII)
(XIV)
(XV)
(XVI) and
(XVII)

Especially preferred are those flavor and fragrance formulations comprising the compound of formula (XIII).

When a compound of formula (I) and/or a compound of formula (II) is used in a flavor and fragrance formulation, then the amount thereof is in the range of 0.0001-10 weight-% (wt-%), related to the total weight of the flavor and fragrance formulation. Preferred is an amount in the range of 0.01-5 wt-%, based on the total weight of the flavor and fragrance formulation.

Therefore the present invention relates to liquid flavor and fragrance formulations comprising
(i) 0.0001-10 wt-% (preferably 0.01-5 wt-%), related to the total weight of the flavor and fragrance, of at least one compound of formula (I) and/or of at least one compound of formula (II).

Therefore the present invention relates to preferred liquid flavor and fragrance formulations comprising
(i) 0.0001-10 wt-% (preferably 0.01-5 wt-%), related to the total weight of the flavor and fragrance, of at least one compound chosen from the group consisting of compounds of formulae (Ia)-(Ih) and (IIa)-(IId).

Therefore the present invention relates to more preferred liquid flavor and fragrance formulations comprising
(i) 0.0001-10 wt-% (preferably 0.01-5 wt-%), related to the total weight of the flavor and fragrance, of at least one compound chosen from the group consisting of compounds of formula (III)-(XVII) (most preferred is the compound of formula (XIV)).

The flavor and fragrance formulations according to the present invention can comprise further ingredients (=auxiliary compounds), such as any further perfuming compounds solvents, adjuvants, thickeners, surface active agents, pigments, extenders, rheology modifiers, dyestuffs, antioxidants, fillers and the like.

Many flavor and fragrance formulations are in a liquid form (like a perfume, cologne, etc.). Therefore, for such liquid formulation a (diluent) solvent is present. Such common diluents are i.e. dipropyleneglycol, isopropylmyristate, triethylcitrate and alcohols (such as ethanol).

Further examples of fine perfumery are Eau de perfume, Eau de Toilette, Eau de Cologne and Splash Cologne. Fine perfumery products are commonly based on an alcoholic solution as diluent. However fine perfumery products using an oil or wax as diluent are also included within the meaning of this invention. The compounds can be employed in widely varying amounts, depending upon the specific application and on the nature and quantity of other odorant ingredients.

When used in a (fine) perfume, the amount is usually between 0.01-10 wt-%, based on the total weight of the (fine) perfume.

However, these values and ranges are given only by way of example, since the experienced perfumer may also achieve effects or may create novel accords with lower or higher concentrations.

Furthermore the present invention relates to liquid flavor and fragrance formulations comprising
(i) at least one compound of formula (I) and/or at least one compound of formula (II), and
(ii) at least one diluent chosen from the group consisting of dipropyleneglycol, isopropylmyristate, triethylcitrate and alcohols (such as ethanol), and optionally
(iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to preferred liquid flavor and fragrance formulations comprising
(i) at least one compound chosen from the group consisting of compounds of formulae (Ia)-(Ih) and (IIa)-(IId), and
(ii) at least one diluent chosen from the group consisting of dipropyleneglycol, isopropylmyristate, triethylcitrate and alcohols (such as ethanol), and optionally
(iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to more preferred liquid flavor and fragrance formulations comprising
(i) at least one compound chosen from the group consisting of compounds of formula (III)-(XVII) (most preferred is the compound of formula (XIV)), and
(ii) at least one diluent chosen from the group consisting of dipropyleneglycol, isopropylmyristate, triethylcitrate and alcohols (such as ethanol), and optionally
(iii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to solid flavor and fragrance formulations comprising (i) at least one compound of formula (I) and/or at least one compound of formula (II), and (ii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to preferred solid flavor and fragrance formulations comprising (i) at least one compound chosen from the group consisting of compounds of formulae (Ia)-(Ih) and (IIa)-(IId), and (ii) at least one auxiliary compound selected from the group consisting of perfuming compounds solvents, adjuvants, thickeners, surface active agents, pigments, extenders, rheology modifiers, dyestuffs, antioxidants and fillers.

Furthermore the present invention relates to more preferred solid flavor and fragrance formulations comprising (i) at least one compound chosen from the group consisting of compounds of formula (III)-(XVII) (most preferred is the compound of formula (XIV)), and (ii) at least one auxiliary compound selected from the group consisting of perfuming compounds solvents, adjuvants, thickeners, surface active agents, pigments, extenders, rheology modifiers, dyestuffs, antioxidants and fillers.

The compounds of formula (I) and the compounds of formula (II) may be used in a broad range of flavor and fragrance formulations, e.g. in any field of fine and functional perfumery, such as perfumes, air care products, household products, laundry products, body care products and cosmetics.

The compounds as described hereinabove may be employed in a flavor and fragrance formulation simply by directly mixing at least one compound of formula (I) and/or at least one compound of formula (II), a mixture thereof, or a fragrance composition with the other ingredients used in the final product, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the other ingredients used in the final product.

Thus, the invention additionally provides a method of manufacturing a flavor and fragrance formulation, comprising the incorporation of at least one compound of formula (I) and/or at least one compound of formula (II), as a fragrance ingredient, either by directly admixing the compound to the other ingredients used in the final product or by admixing a fragrance composition comprising at least one compound of formula (I) and/or at least one compound of formula (II), which may then be mixed with the other ingredients used in the final product, using conventional techniques and methods.

Thus, the invention additionally provides a preferred method of manufacturing a flavor and fragrance formulation, comprising the incorporation of at least one compound chosen from the group consisting of compounds of formulae (Ia)-(Ih) and (IIa)-(IId), as a fragrance ingredient, either by directly admixing the compound to the other ingredients used in the final product or by admixing a fragrance composition comprising at least one compound chosen from the group consisting of compounds of formulae (Ia)-(Ih) and (IIa)-(IId), which may then be mixed with the other ingredients used in the final product, using conventional techniques and methods.

Thus, the invention additionally provides a more preferred method of manufacturing a flavor and fragrance formulation, comprising the incorporation of at least one compound chosen from the group consisting of compounds of formula (III)-(XVII) (most preferred is the compound of formula (XIV)), as a fragrance ingredient, either by directly admixing the compound to the other ingredients used in the final product or by admixing a fragrance composition comprising at least one compound chosen from the group consisting of compounds of formula (III)-(XVII) (most preferred is the compound of formula (XIV)), which may then be mixed with the other ingredients used in the final product, using conventional techniques and methods.

Through the addition of an olfactory acceptable amount of a compound of the present invention as hereinabove described, or a mixture thereof, the odor notes of a consumer product base will be improved, enhanced or modified.

Thus, the invention furthermore provides a method for improving, enhancing or modifying a consumer product (=final product) base by means of the addition thereto of an olfactory acceptable amount of at least one compound of formula (I) and/or at least one compound of formula (II).

Thus, the invention furthermore provides a preferred method for improving, enhancing or modifying a consumer product (=final product) base by means of the addition thereto of an olfactory acceptable amount of at least one compound chosen from the group consisting of compounds of formulae (Ia)-(Ih) and (IIa)-(IId).

Thus, the invention furthermore provides a more preferred method for improving, enhancing or modifying a consumer product (=final product) base by means of the addition thereto of an olfactory acceptable amount of at least one compound chosen from the group consisting of compounds of formula (III)-(XVII) (most preferred is the compound of formula (XIV)).

In the context of the present invention the olfactory effective amount is to be understood as the amount of the at least one compound of formula (I) and/or of the at least one compound of formula (II) in a flavor and fragrance formulation will contribute to its particular olfactory characteristics, but the olfactory effect of the flavor and fragrance formulation will be the sum of the effects of each of the perfumes or fragrance ingredients. Thus the compounds of the invention can be used to alter the aroma characteristics of the flavor and fragrance formulation, or by modifying the olfactory reaction contributed by another ingredient in the composition. The amount will vary depending on many factors including other ingredients, their relative amounts and the effect that is desired.

As used herein, "consumer product (=final product)" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body care products, e.g. shampoo, shower gel; air care products and cosmetics, e.g. deodorant, vanishing creme. This list of products is given by way of illustration and is not to be regarded as being in any way limiting.

The compounds of formula (I) and the compounds of formula (II) may be prepared using methods known to the person skilled in the art of organic synthesis.

Furthermore the present invention relates to the following compounds of formulae (IV), (V), (VI), (VII), (IX), (X), (XI) and (XII) which are novel compounds

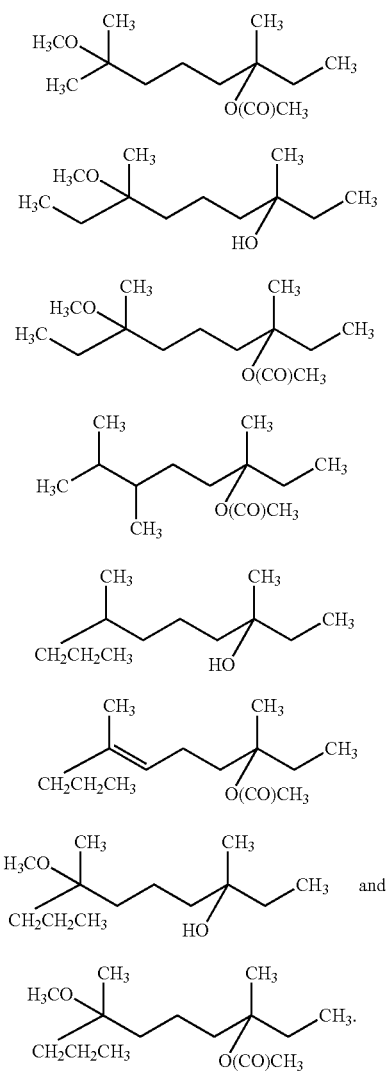

Thus, the present invention is also directed to their synthesis as shown in FIG. 1.

The invention is now further illustrated in the following non-limiting examples.

EXAMPLES

All compounds were evaluated by a panel of four persons for their intensity whereby a range of 1 to 10 was used (1=very low intensity; 10=very high intensity). Furthermore these four persons also described the odor of the compounds. The tenancy was evaluated by one person after 3, 6, 8, 24, 48, 72 and 96 hours. For such evaluations a piece of paper was immersed in each single liquid compound as such.

Example 1

Manufacture and olfactory properties of the compound of formula III
(7-methoxy-3,7-dimethyl-octan-3-ol)

a) Manufacture of 6-methoxy-6-methyl-2-heptanon by methoxylation of 6-methyl-5-hepten-2-on 6000.0 g of 6-methyl-5-hepten-2-on and 9480.0 g of methanol are mixed in a reactor and cooled to 0° C. 4507.8 g of $H_2SO_4$ (96 weight-%) are added within 40 minutes by keeping the temperature. The reaction mixture is then heated up to 30° C. After 5 hours the reaction mixture is poured on ice water and extracted with methyl tert-butyl ether. The combined methyl tert-butyl ether phases are washed with 20 weight-% aqueous $Na_2CO_3$ solution and concentrated NaCl solution. The solvent is removed from the organic phase and the residue distilled (10 mbar; 130° C.) to yield 6-methoxy-6-methyl-2-heptanon.

b) Manufacture of 7-methoxy-3,7-dimethyl-1-octin-3-ol by ethinylation of 6-methoxy-6-methyl-2-heptanon 2566.4 g of 6-methoxy-6-methyl-2-heptanon are put in an autoclave under nitrogen and cooled down to a temperature of 15° C. 5221.0 g of ammonia ($NH_3$) are added. The reaction mixture is cooled again to 15° C. Then acetylene ($C_2H_2$) is added. The reaction mixture is cooled again to 15° C. Then 52.8 g of a 40 weight % aqueous potassium hydroxide (KOH) solution are added continuously. After the end of the reaction the reaction mixture is neutralized with acetic acid, extracted with water and the solvent removed. The resulting raw product is then distilled to obtain 7-methoxy-3,7-dimethyl-1-octin-3-ol.

c) Manufacture of 7-methoxy-3,7-dimethyl-octan-3-ol by hydrogenation of 7-methoxy-3,7-dimethyl-1-octin-3-ol 404.83 g of 7-methoxy-3,7-dimethyl-1-octin-3-ol and 1.00 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 130° C.) to obtain the compound of formula III.

d) Olfactory Properties

Odor description: very little camphor; chemical; pharmaceutical; medical; gum; herbs; swimming pool.
Intensity: 4.
Tenancy: 24-48 hours.

Example 2

Manufacture and Olfactory Properties of the Compound of Formula IV 7-methoxy-3,7-dimethyl-1-octin-3-ol is manufactured as already described in example 1 a) and b).

a) Manufacture of 7-methoxy-3,7-dimethyl-1-octin-3-yl acetate 560.0 g of 7-methoxy-3,7-dimethyl-1-octin-3-ol and 0.49 g of p-toluene sulfonic acid in water are mixed and heated up to a temperature of 40° C. 372.5 g of acetic acid anhydride are added within 2 hours. After ca. 20 hours the reaction mixture is cooled down and distilled to obtain 7-methoxy-3,7-dimethyl-1-octin-3-yl acetate.

b) Manufacture of the compound of formula (IV) by hydrogenation of 7-methoxy-3,7-dimethyl-1-octin-3-yl acetate 373.56 g of 7-methoxy-3,7-dimethyl-1-octin-3-yl acetate and 0.80 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 135° C.) to obtain the compound of formula (IV).

c) Olfactory Properties

Odor description: drugstore; pharma odor.
Intensity: 2.
Tenancy: 8-24 hours.

Example 3

Manufacture and Olfactory Properties of the Compound of Formula V a) Manufacture of 6-methoxy-6-methyl-2-octanon by methoxylation of 6-methyl-5-octen-2-on 6600.0 g of 6-methyl-5-octen-2-on and 9390.0 g of methanol are mixed in a reactor and cooled to 0° C. 4462.8 g of $H_2SO_4$ (96 weight-%) are added within 40 minutes by keeping the temperature. The reaction mixture is then heated up to 30° C. After 5 hours the reaction mixture is poured on ice water and extracted with methyl tert-butyl ether. The combined methyl tert-butyl ether phases are washed with 20 weight-% aqueous $Na_2CO_3$ solution and concentrated NaCl solution. The solvent is removed from the organic phase and the residue distilled (5 mbar; 125° C.) to yield 6-methoxy-6-methyl-2-octanon.

b) Manufacture of 7-methoxy-3,7-dimethyl-1-nonin-3-ol by ethinylation of 6-methoxy-6-methyl-2-octanon 1265.0 g of 6-methoxy-6-methyl-2-octanon are put in an autoclave under nitrogen and cooled down to a temperature of 15° C. 3226.0 g of ammonia ($NH_3$) are added. The reaction mixture is cooled again to 15° C. Then acetylene ($C_2H_2$) is added. The reaction mixture is cooled again to 15° C. Then 33.0 g of a 40 weight-% aqueous potassium hydroxide (KOH) solution are added continuously. After the end of the reaction the reaction mixture is neutralized with acetic acid, extracted with water and the solvent removed. The resulting raw product is then distilled to obtain 7-methoxy-3,7-dimethyl-1-nonin-3-ol.

c) Manufacture of 7-methoxy-3,7-dimethyl-nonan-3-ol by hydrogenation of 7-methoxy-3,7-dimethyl-1-nonin-3-ol 304.68 g of 7-methoxy-3,7-dimethyl-1-nonin-3-ol and 0.80 g of 5% Pd on carbon (Pd/C) are put in an autoclave under nitrogen and heated to a temperature of 40° C. under stirring. Then the nitrogen is exchanged by hydrogen and put to an absolute pressure of 2 bar. After the calculated amount of hydrogen has been consumed the reaction mixture is filtered and distilled (2 mbar, 140° C.) to obtain the compound of formula (V).

d) Olfactory Properties

Odour description: forest soil; fir tree; pleasant.
Intensity: 3.5.
Tenancy: 48-72 hours.

Example 4

Manufacture and Olfactory Properties of the Compound of Formula VI 7-methoxy-3,7-dimethyl-1-nonin-3-ol is manufactured as already described in example 3 a) and b).

a) Manufacture of 7-methoxy-3,7-dimethyl-1-nonin-3-yl acetate by acylation of 7-methoxy-3,7-dimethyl-1-nonin-3-ol 707.0 g of 7-methoxy-3,7-dimethyl-1-nonin-3-ol and 0.57 g of p-toluene sulfonic acid in water are mixed and heated up to a temperature of 60° C. 437.1 g of acetic acid anhydride are added within 2 hours. After ca. 20 hours the reaction mixture is cooled down and distilled to obtain 7-methoxy-3,7-dimethyl-1-nonin-3-yl acetate.

b) Manufacture of the compound of formula (VI) by hydrogenation of 7-methoxy-3,7-dimethyl-1-nonin-3-yl acetate 292.26 g of 7-methoxy-3,7-dimethyl-1-nonin-3-yl acetate and 0.80 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 140° C.) to obtain the compound of formula (VI).

c) Olfactory Properties

Odor description: wet carton; metallic; chemical; pharmaceutical; very, very little natural resin; fir; new clothes.
Intensity: 2.5.
Tenancy: 24-48 hours.

Example 5

Manufacture and Olfactory Properties of the Compound of Formula VII 3,6,7-Trimethyl-6-octen-1-in-3-ol may be prepared by ethinylation of 5,6-dimethyl-5-hepten-2-on.

a) Manufacture of 3,6,7-trimethyl-6-octen-1-in-3-ylacetate by acylation of 3,6,7-trimethyl-6-octen-1-in-3-ol 650.0 g of 3,6,7-trimethyl-6-octen-1-in-3-ol and 0.63 g of p-toluene sulfonic acid in water are mixed and heated up to a temperature of 40° C. 479.3 g of acetic acid anhydride are added within 2 hours. After ca. 20 hours the reaction mixture is cooled down and distilled to obtain 3,6,7-trimethyl-6-octen-1-in-3-yl acetate.

b) Manufacture of the compound of formula (VII) by hydrogenation of 3,6,7-trimethyl-6-octen-1-in-3-yl acetate 444.0 g of 3,6,7-trimethyl-6-octen-1-in-3-yl acetate and 1.2 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 120° C.) to obtain the compound of formula (VII).

c) Olfactory Properties

Odor description: melon; light; fresh; baby powder.
Intensity: 4.5.
Tenancy: 6-8 hours.

Example 6

Manufacture and Olfactory Properties of the Compound of Formula VIII a) Manufacture of 6-methyl-2-nonanon by hydrogenation of 6-methyl-5-nonen-2-on 900.0 g of 6-methyl-5-nonen-2-on and 1.60 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (10 mbar, 120° C.) to obtain 6-methyl-2-nonanon.

b) Manufacture of 3,7-dimethyl-1-decin-3-ol by ethinylation of 6-methyl-2-nonanon 760.0 g of 6-methyl-2-nonanon are put in an autoclave under nitrogen and cooled down to a temperature of 15° C. 1305.0 g of ammonia ($NH_3$) are added. The reaction mixture is cooled again to 15° C. Then acetylene ($C_2H_2$) is added. The reaction mixture is cooled again to 15° C. Then 14.0 g of a 40 weight-% aqueous potassium hydroxide (KOH) solution are added continuously. After the end of the reaction the reaction mixture is neutralized with acetic acid, extracted with water and the solvent removed. The resulting raw product is then distilled to obtain 3,7-dimethyl-1-decin-3-ol.

c) Manufacture of 3,7-dimethyl-1-decin-3-ylacetate 472.0 g of 3,7-dimethyl-1-decin-3-ol and 0.42 g of p-toluene sulfonic acid in water are mixed and heated up to a temperature of 40° C. 317.4 g of acetic acid anhydride are added within 2 hours. After ca. 20 hours the reaction mixture is cooled down and distilled to obtain 3,7-dimethyl-1-decin-3-yl acetate.

d) Manufacture of the compound of formula (VIII) by hydrogenation of 3,7-dimethyl-1-decin-3-ylacetate 162.0 g of 3,7-dimethyl-1-decin-3-yl acetate and 0.20 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 140° C.) to obtain the compound of formula (VIII).

e) Olfactory Properties

Odor description: grain/cereal; flour.
Intensity: 4.
Tenancy: 8-24 hours.

Example 7

Manufacture and Olfactory Properties of the Compound of Formula IX a) Manufacture of 3,7-dimethyl-6-decen-1-in-3-ol by ethinylation of 6-methyl-5-nonen-2-on 1360.0 g of 6-methyl-5-nonen-2-on are put in an autoclave under nitrogen and cooled down to a temperature of 15° C. 2548.0 g of ammonia ($NH_3$) are added. The reaction mixture is cooled again to 15° C. Then acetylene ($C_2H_2$) is added. The reaction mixture is cooled again to 15° C. Then 26.4 g of a 40 weight-% aqueous potassium hydroxide (KOH) solution are added continuously. After the end of the reaction the reaction mixture is neutralized with acetic acid, extracted with water and the solvent removed. The resulting raw product is then distilled to obtain 3,7-dimethyl-6-decen-1-in-3-ol.

b) Manufacture of the compound of formula (IX) by hydrogenation of 3,7-dimethyl-6-decen-1-in-3-ol 220.0 g of 3,7-dimethyl-6-decen-1-in-3-ol and 0.50 g of 5% Pd on carbon (Pd/C) are put in an autoclave under nitrogen and heated to a temperature of 60° C. under stirring. Then the nitrogen is exchanged by hydrogen and put to an absolute pressure of 2 bar. After the calculated amount of hydrogen has been consumed the reaction mixture is filtered and distilled (2 mbar, 130° C.) to obtain the compound of formula (IX).

c) Olfactory Properties

Odor description: dusty; green.
Intensity: 4.5.
Tenancy: 8-24 hours.

Example 8

Manufacture and Olfactory Properties of the Compound of Formula X 3,7-Dimethyl-6-decen-1-in-3-ol is prepared as described in example 7 a).

a) Manufacture of 3,7-dimethyl-6-decen-1-in-3-yl acetate by acylation of 3,7-dimethyl-6-decen-1-in-3-ol 609.0 g of 3,7-dimethyl-6-decen-1-in-3-ol and 0.54 g of p-toluene sulfonic acid in water are mixed and heated up to a temperature of 40° C. 414.1 g of acetic acid anhydride are added within 2 hours. After ca. 20 hours the reaction mixture is cooled down and distilled to obtain 3,7-dimethyl-6-decen-1-in-3-yl acetate.

b) Manufacture of the compound of formula (X) by hydrogenation of 3,7-dimethyl-6-decen-1-in-3-yl acetate 239.0 g of 3,7-dimethyl-6-decen-1-in-3-yl acetate, 6.5 g of Lindlar catalyst (5% Pd+3.5% Pb on $CaCO_3$) and 0.28 g of zinc acetate are put in an autoclave and heated under nitrogen to a temperature of 40° C. Nitrogen is exchanged by hydrogen ($H_2$) and the reaction mixture put at an absolute pressure of 2 bar. After the calculated amount of hydrogen has been consumed the reaction mixture is filtered and distilled (2 mbar, 140° C.) to obtain 3,7-dimethyl-6-decen-3-yl acetate (=compound of formula X).

c) Olfactory Properties

Odor description: broad-leaved forest; green grass.
Intensity: 2.5.
Tenancy: 8-24 hours.

Example 9

Manufacture and Olfactory Properties of the Compound of Formula XI a) Manufacture of 6-methoxy-6-methyl-nonan-2-on by methoxylation of 6-methyl-5-nonen-2-on 6404.0 g of 6-methyl-5-nonen-2-on, 10400.0 g of methanol and 2050.0 g of Amberlyst 15 wet are mixed in a reactor and heated up to 80° C. After 15 hours the reaction mixture is cooled and reduced in volume by distilling. The remaining residue is then distilled (2 mbar; 145° C.) to give 6-methoxy-6-methyl-nonan-2-on.

b) Manufacture of 7-methoxy-3,7-dimethyl-1-decin-3-ol by ethinylation of 6-methoxy-6-methyl-2-nonanon 1020.0 g of 6-methoxy-6-methyl-2-nonanon are put in an autoclave under nitrogen and cooled down to a temperature of 15° C. 1931.0 g of ammonia ($NH_3$) are added. The reaction mixture is cooled again to 15° C. Then acetylene ($C_2H_2$) is added. The reaction mixture is cooled again to 15° C. Then 19.8 g of a 40 weight % aqueous potassium hydroxide (KOH) solution are added continuously. After the end of the reaction the reaction mixture is neutralized with acetic acid, extracted with water and the solvent removed. The resulting raw product is then distilled to obtain 7-methoxy-3,7-dimethyl-1-decin-3-ol.

c) Manufacture of the compound of formula (XI) by hydrogenation of 7-methoxy-3,7-dimethyl-1-decin-3-ol 220.0 g of 7-methoxy-3,7-dimethyl-1-decin-3-ol and 0.25 g of 5% Pd on carbon (Pd/C) are put in an autoclave under nitrogen and heated to a temperature of 45° C. under stirring. Then the nitrogen is exchanged by hydrogen and put to an absolute pressure of 2 bar. After the calculated amount of hydrogen has been consumed the reaction mixture is filtered and distilled (2 mbar, 140° C.) to obtain the compound of formula (XI) (=7-methoxy-3,7-dimethyl-3-decanol).

d) Olfactory Properties

Odor description: melon; citrus.
Intensity: 3.
Tenancy: 48-72 hours.

Example 10

Manufacture and Olfactory Properties of the Compound of Formula XII

7-Methoxy-3,7-dimethyl-1-decin-3-ol is prepared as described in example 9 a) and b).

a) Manufacture of 7-methoxy-3,7-dimethyl-1-decin-3-yl acetate by acylation of 7-methoxy-3,7-dimethyl-1-decin-3-ol 430.0 g of 7-Methoxy-3,7-dimethyl-1-decin-3-ol and 0.32 g of p-toluene sulfonic acid in water are mixed and heated up to a temperature of 40° C. 248.3 g of acetic acid anhydride are added within 2 hours. After ca. 20 hours the reaction mixture is cooled down and distilled to obtain 7-methoxy-3,7-dimethyl-1-decin-3-yl acetate.

b) Manufacture of the compound of formula (XII) by hydrogenation of 7-methoxy-3,7-dimethyl-1-decin-3-yl acetate 190.0 g of 7-methoxy-3,7-dimethyl-1-decin-3-yl acetate and 1.5 g of 5% Pd on carbon (Pd/C) are put in an autoclave under nitrogen and heated to a temperature of 45° C. under stirring. Then the nitrogen is exchanged by hydrogen and put to an absolute pressure of 2 bar. After the calculated amount of hydrogen has been consumed the reaction mixture is filtered and distilled (1 mbar, 150° C.) to obtain the compound of formula (XII) (=7-methoxy-3,7-dimethyl-3-decanyl acetate).

c) Olfactory Properties

Tenancy: 48-72 hours.

Example 11

Olfactory Properties of the Compound of Formula XIII

Odor description: dry wood with water (sauna); warm aspect; dusty; old flannel; sweety.
Intensity: 5.
Tenancy: 6-8 hours.

Example 12

Olfactory Properties of the Compound of Formula XIV

Odor description: flowery; citrus; fresh; washing agent; rotten wood; olibanum.
Intensity: 6.5.
Tenancy: 3-6 hours.

Example 13

Olfactory Properties of the Compound of Formula XV

Odor description: soil; mushroom; flowery; dusty.
Intensity: 4.5.
Tenancy: 6-8 hours.

Example 14

Olfactory Properties of the Compound of Formula XVI

Odor description: tropical fruits; pleasant.
Intensity: 4.5.
Tenancy: 3-6 hours.

Example 15

Olfactory Properties of the Compound of Formula XVII

Odour description: dusty, dry.
Intensity: 4.
Tenancy: 8-24 hours.

The invention claimed is:

1. A flavor and fragrance formulation comprising 0.0001 to 10 wt %, relative to total weight of the flavor and fragrance formulation, of at least one compound of formula (II):

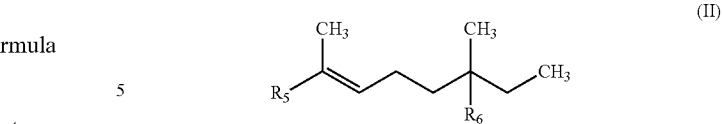

$R_5$ signifies —$CH_2CH_2CH_3$; and
R6 signifies —OH or $O(CO)CH_3$.

2. The flavor and fragrance formulation according to claim 1, wherein the flavor and fragrance formulation is a solid, gel or liquid.

3. The flavor and fragrance formulation according to claim 1, wherein the flavor and fragrance formulation is selected from the group consisting of a perfumes, hair care products, household products, laundry products, body care products and cosmetic products.

4. The flavor and fragrance formulation according to claim 1, wherein the at least one compound of formula (II) is present in an amount of 0.01-5 wt-%, based on the total weight of the flavor and fragrance formulation.

5. The flavor and fragrance formulation according to claim 1, further comprising at least one auxiliary compound selected from the group consisting of solvents, adjuvants, thickeners, surface active agents, pigments, extenders, rheology modifiers, dyestuffs, antioxidants and fillers.

6. A compound of formula (X):

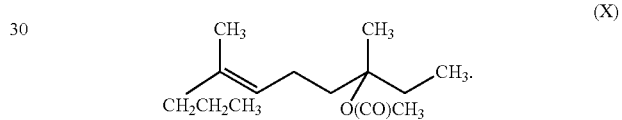

* * * * *